(12) United States Patent
Kuebler et al.

(10) Patent No.: US 7,845,798 B2
(45) Date of Patent: Dec. 7, 2010

(54) OPHTHALMIC SURGICAL SYSTEM

(75) Inventors: Christoph Kuebler, Oberkochen (DE);
Daniel Bublitz, Jena (DE); Markus Seesselberg, Aalen (DE)

(73) Assignees: Carl Zeiss Surgical GmbH, Oberkochen (DE); Carl Zeiss AG, Oberkochen (DE)

( * ) Notice: Subject to any disclaimer, the term of this patent is extended or adjusted under 35 U.S.C. 154(b) by 0 days.

(21) Appl. No.: 12/644,746

(22) Filed: Dec. 22, 2009

(65) Prior Publication Data

US 2010/0157246 A1 Jun. 24, 2010

(30) Foreign Application Priority Data

Dec. 23, 2008 (DE) .................. 10 2008 062 908

(51) Int. Cl.
*A61B 3/10* (2006.01)
(52) U.S. Cl. ...................... 351/221; 351/215
(58) Field of Classification Search .......... 351/221, 351/205, 106, 246, 200, 215, 214; 359/459, 359/385, 497, 502; 349/8, 9, 20; 353/31
See application file for complete search history.

(56) References Cited

U.S. PATENT DOCUMENTS

| 6,307,688 | B1 | 10/2001 | Merz et al. |
| 7,295,371 | B1 * | 11/2007 | Sedlmayr ................ 359/495 |
| 2005/0241653 | A1 | 11/2005 | Van Heugten et al. |

| 2008/0062384 | A1 | 3/2008 | Rombach |

FOREIGN PATENT DOCUMENTS

| DE | 44 13 920 B4 | 7/2004 |
| DE | 10 2005 031 496 B4 | 1/2007 |
| DE | 10 2007 042 571 A1 | 4/2008 |
| DE | 10 2008 047 400 A1 | 4/2010 |

OTHER PUBLICATIONS

Bille et al., "The Development of Wavefront Technology and its Application to Ophthalmology"; *Aberration-Free Refractive Surgery: New Frontiers in Vision*, 2nd Enlarged Edition, Springer, 2004, Chapter 1, pp. 1-20.

(Continued)

*Primary Examiner*—Hung X Dang
(74) *Attorney, Agent, or Firm*—Townsend and Townsend and Crew LLP

(57) ABSTRACT

A system includes an optical system having two beam splitters (a dichroic beam splitter and a polarizing beam splitter), which are designed to provide three separate beam paths for observing an object. The dichroic beam splitter is designed to separate two beam paths depending on the wavelength of the light of the respective beam path. The polarizing beam splitter is designed such that two beam paths are separated depending on a direction of polarization of the light of the respective beam path. The measuring light is linearly polarized after having passed the polarizing beam splitter and may be influenced with respect to the state of polarization by a retarding plate. The returning measuring light incident on the polarizing beam splitter is linearly polarized and also polarized in such a direction that the returning measuring light is transported through the polarizing beam splitter towards the analyzing detector with a high efficiency.

21 Claims, 4 Drawing Sheets

OTHER PUBLICATIONS

Chalita et al., "Shack-Hartmann Aberrometry: Historical Principles and Clinical Applications", In: Krueger R, Applegate R, MacRae S, eds., *Wavefront Customized Visual Correction: the Quest for Super Vision II*. Thorofare: SLACK Inc, 2004, Chapter 15, pp. 127 to 130.

"Jones Calculus" retrieved from the Internet: <www.fourieroptics.org.ukjones.html> on May 4, 2010, 4 pages total.

Roorda, "A review of basic wavefront optics" In: Krueger R, Applegate R, MacRae S, eds., *Wavefront Customized Visual Correction: the Quest for Super Vision II*. Thorofare: SLACK Inc, 2004, Chapter 2, pp. 9-19.

Sharma, "Polarization of Light Waves", *Optics Principles and Application*, Academic Press, 2006, Chapter 3, pp. 121-157.

Smith et al., "The Eye and Visual Optical Instruments", Cambridge University Press, 1997, Chapter 31, pp. 585-594.

Thibos et al., "Assessment of Optical Quality" In: Krueger R, Applegate R, MacRae S, eds., *Wavefront Customized Visual Correction: the Quest for Super Vision II*. Thorofare: SLACK Inc, 2004, Chapter 6, pp. 55-63.

WASCA Analyzer User Manual, Carl Zeiss Meditec AG, Jena, 2005, 96 pages total.

Yoon et al., "Optimizing the Shack-Hartmann Wavefront Sensor", Wavefront Customized Visual Correction, In: Krueger R, Applegate R, MacRae S, eds., *Wavefront Customized Visual Correction: the Quest for Super Vision II*. Thorofare: SLACK Inc, 2004, Chapter 16, pp. 131-136.

* cited by examiner

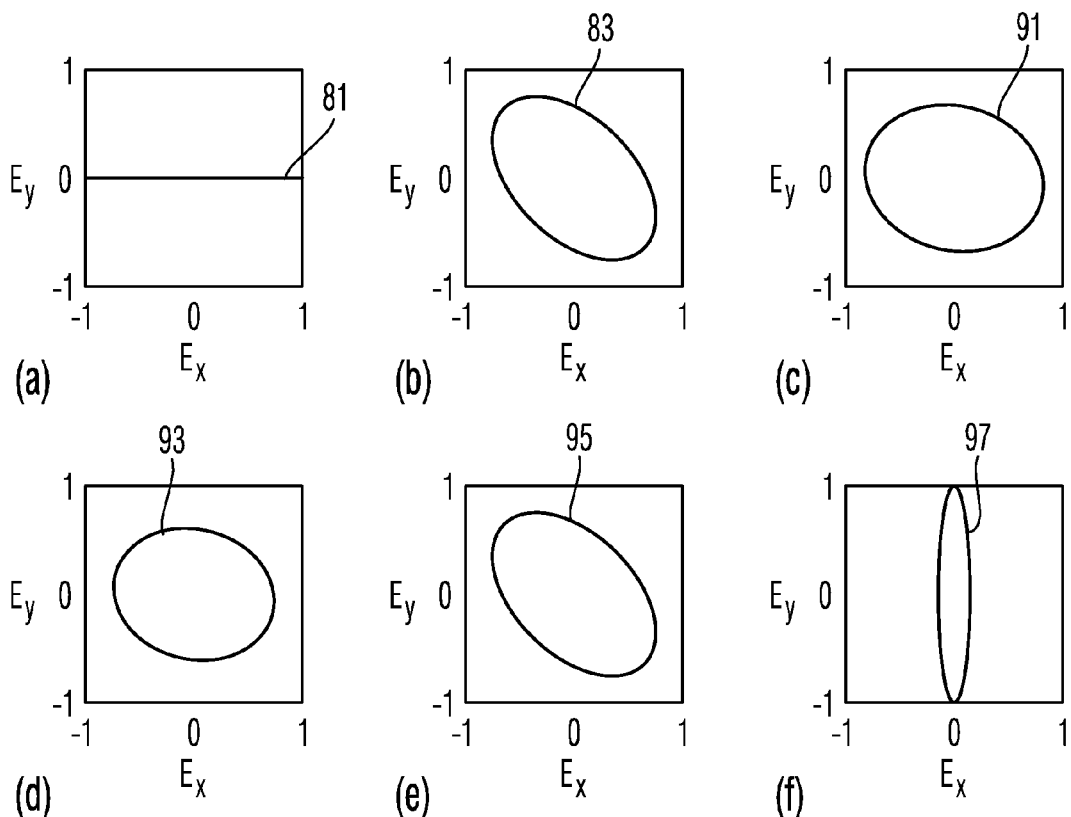
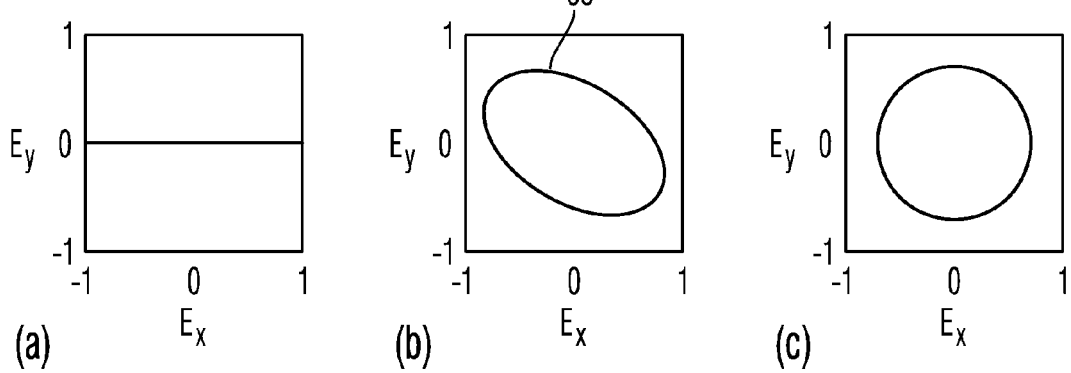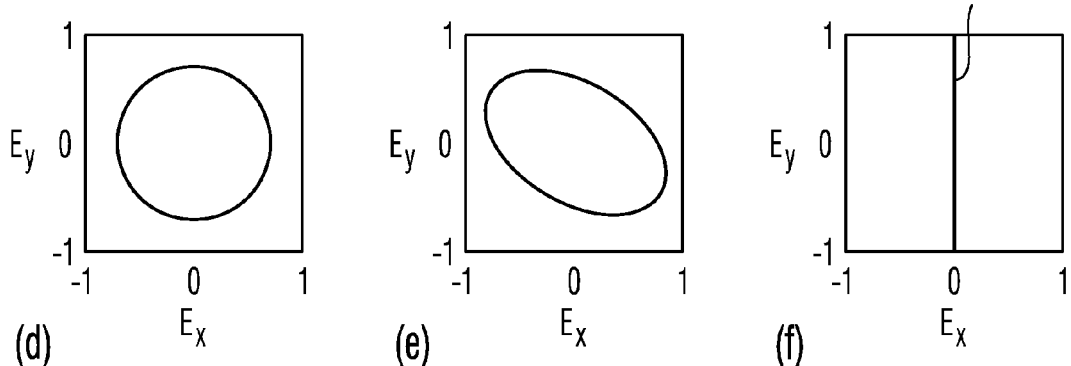

OPHTHALMIC SURGICAL SYSTEM

CROSS-REFERENCES TO RELATED APPLICATIONS

The present application claims priority to German Patent Application No. 10 2008 062 908.1, filed Dec. 23, 2008, entitled "Ophthalmic Surgical System," the contents of which is hereby incorporated by reference in its entirety.

BACKGROUND OF THE INVENTION

The invention relates to ophthalmic surgical systems such as ophthalmic surgical microscopes, in which there is provided a measuring beam path, such as a wavefront measuring beam path.

Ophthalmic surgical systems which comprise an ophthalmic surgical microscope in which a wave front sensor is implemented within the beam path are commonly known. Such commonly known surgical systems provide an optical system having three optical paths. A first beam path is an observation beam path of visible light, which passes through an microscope optical system, which comprises an objective lens and oculars. In this way, by viewing into the oculars, a user can observe an object such as an eye, which has to undergo cataract surgery. The optical system further provides a second beam path, in which there is arranged a wavefront sensor for analyzing wavefronts emanating from the eye under surgery. The optical system further provides a third beam path for directing measuring light, generated by a light source, into the direction of the eye under surgery. The measuring light which returns from the eye is detected by the wavefront sensor. For separating the first beam path from the second beam path, the optical system further comprises a beam splitter. The optical system further comprises a polarizing beam splitter for separating the second beam path from the third beam path. The measuring light is transformed by a quarter-wave plate into circularly polarized light, which is reflected at the eye by keeping the circular polarization. Thereafter, the quarter-wave plate is again traversed by the measuring light, whereby the measuring light is converted into light with linear polarization. This direction of polarization is oriented orthogonally relative to the direction of polarization of the measuring light which is directed to the object. Thereby, the measuring light is guide by the polarizing beam splitter to the wave front detector with a high efficiency.

However, experience has shown that such systems yield insufficient results when detecting with the wavefront sensor.

SUMMARY OF THE INVENTION

The present invention has been accomplished taking the above problems into consideration.

Accordingly, it is an object to provide an ophthalmic surgical system, with an increased efficiency of detection of measuring light.

In an embodiment, there is provided a system having an optical system, which comprises two beam splitters which are designed to provide three separate beam paths for observing an object.

According to embodiments, the two beam splitters comprise a dichroic beam splitter and a polarizing beam splitter.

The dichroic beam splitter is designed to separate two beam paths depending on the wavelength of the light of the respective beam path. Thereby, for example, light of a first wavelength traverses the dichroic beam splitter and light of a second wavelength is reflected at the dichroic beam splitter.

In particular, the dichroic beam splitter may be designed such that a first range of wavelengths of the system traverses the dichroic beam splitter and a second range of wavelengths of the system is reflected at the beam splitter. The first range of wavelength and the second range of wavelength may be non-identical. In particular, the first range of wavelengths and the second range of wavelengths may be non-overlapping.

The polarizing beam splitter is designed such that two beam paths are separated depending on a direction of polarization of the light of the respective beam path. Thereby, for example, light, which has a direction of polarization in a first direction linearly traverses the beam splitter, whereas light having a direction of polarization, which is oriented orthogonally relative to the first direction, is reflected at the polarizing beam splitter.

According to embodiments, the system is designed such that an illumination beam path is separated from an analyzing beam path by a polarizing beam splitter. The illumination beam path is designed such that measuring light is transported from the light source to the object. The analyzing beam path is designed such that measuring light is transported from the object to a measuring light detector, which may be a wavefront detector.

The measuring light, which is traveling to the object, is linearly polarized after having passed the polarizing beam splitter and may be influenced with respect to the state of polarization by a retarding plate, which is arranged between the polarizing beam splitter and the object. Thereby, the measuring light, which is incident on the object, is circularly or elliptically polarized. The measuring light, which returns from the object, also comprises circularly or elliptically polarized light. The returning measuring light again traverses the retarding plate.

Thereby, the returning measuring light is influenced such that when incident on the polarizing beam splitter, the returning measuring light is linearly polarized as much as possible and also polarized as much as possible in such a direction that the returning measuring light is transported through the polarizing beam splitter towards the analyzing detector with an efficiency as high as possible.

According to embodiments, the retarding plate comprises a birefringent material. The birefringent material is arranged in the beam path such that the beam path is not divided by the birefringent nature of the retarding plate. This is the case when the so-called extraordinary axis of the birefringent material is arranged orthogonal to the direction of the beam path. The extraordinary axis may be defined as the fast axis of the birefringent material. In this case, the birefringent material provides for two directions of polarizations, which are oriented orthogonal to each other, different optical path lengths, i.e. a relative phase difference between said two directions of polarization. According to an embodiment, the retarding plate is designed such that said phase difference does not have values of exactly $\lambda/4$, $3\lambda/4$, $5\lambda/4$, etc.

According to embodiments, the retarding plate provides for light, which traverses said retarding plate a phase difference, which satisfies:

$$(2m)\lambda/4+\delta \leq \phi \leq (2m+1)\lambda/4-\delta,$$

wherein $\lambda$ is a wavelength of the light, $\phi$ is the phase difference m is an integer, and $\delta$ represents a value greater than $0.05*\lambda/4$ and less than $\lambda/8$.

According to further embodiments, the lower limit of the range of values for λ is 0.1 times λ/4, or 0.15 times λ/4, or 0.2 times λ/4.

According to further embodiments, the extraordinary axis of the birefringent material is oriented relative to directions of polarization of the light which traverses or is reflected at the polarizing beam splitter such that the extraordinary axis is not oriented parallel or orthogonal to the direction of polarization of said light.

According to embodiments, the extraordinary axis of the birefringent material has an angle relative to the direction of polarization of the light, which traverses or is reflected at the polarizing beam splitter, wherein said angle satisfies:

$$(2n+1)*45°+\epsilon \leq \beta \leq (2n+3)*45°-\epsilon$$

wherein

β represents the angle, n represents an integer, and

ε represents a value greater than 4° and less than 45°.

The values of β may further not match values of 0°, 90°, 180°, 270°, etc.

According to exemplary embodiments, the lower limit for the range of values for ε has a value of 6°, 8° or 10°.

The design rules described above for the optical properties of the retarding plate can advantageously be used to optimize the beam paths, which traverse or which are reflected at the polarizing beam splitter, with respect to their intensities. For example, said beam paths may be optimized such that measuring light, which returns from the eye, can reach the analyzing detector with a high intensity. In particular, this can be advantageous in case further optical elements are implemented in the beam path which influence the state of polarization of the light of the divided beam paths generated by the polarizing beam splitter.

According to embodiments, such an optical element, which influences the state of polarization of the light may be a dichroic beam splitter. The dichroic beam splitter may be designed such that the separated beam paths, which are generated by the polarizing beam splitter, are separated from one or more further beam paths. According to further specific embodiments, the dichroic beam splitter is designed to separate the measuring beam paths, which traverse or are reflected at the polarizing beam splitter from an observation beam path, which is configured to generate an image of the object with visible light. The measuring light may comprise light of wavelengths, which are different from wavelengths of visible light.

According to embodiments, the optical system comprises an objective lens, which may comprise one or more lens elements. The optical system may further comprise one of one or more oculars and/or one or more cameras, which are designed to display an image of the object to a user.

According to exemplary embodiments, there is provided a measuring light detector in one of the beam paths, in which the polarizing beam splitter is arranged. In other words, the measuring light detector may be arranged in the beam path, which is reflected at the polarizing beam splitter or in the beam path, which traverses the polarizing beam splitter. According to exemplary embodiments, the measuring light detector comprises a wavefront sensor, which, for example, may be an Harmann-Shack type sensor.

According to embodiments, there are provided one or a plurality of lenses in the measuring beam path between the polarizing beam splitter and the object, wherein said one or plurality of lenses are designed to achieve a predetermined shape (in particular a predetermined collimation and/or cross-section) of the measuring beam. According to an exemplary embodiment, said plurality of lenses have the configuration of a Kepler telescope or a Galilei telescope.

According to an exemplary embodiment, the retarding plate is arranged between the one or plurality of lenses and the dichroic beam splitter, wherein the dichroic beam splitter is designed to separate the measuring beam paths from one or more further beam paths provided in the system.

According to further embodiments the retarding plate may be arranged between the polarizing beam splitter and the one or plurality of lenses, or between the dichroic beam splitter and the object. The retarding plate may also be arranged between two of the plurality of lenses.

According to embodiments, the measuring beam paths are reflected at the dichroic beam splitter. According to exemplary embodiments, the dichroic beam splitter comprises a transparent plate, which comprises a dielectric reflecting coating for the measuring light. The dielectric reflecting coating may be disposed on a surface of the transparent plate. According to a further specific embodiment, the dielectric reflecting coating on the transparent plate is designed such that the measuring light is reflected at the coating without traversing the transparent plate.

According to an embodiment, there is provided a surgical microscope having an objective lens and at least a pair of stereoscopic beam paths, which are designed to provide a stereoscopic image of the object. The objective lens may comprise one or more lens elements. The surgical microscope further comprises a measuring beam path, which is reflected at a mirror, in particular at the dichroic beam splitter, such that the measuring beam path is oriented into the direction of the object. Said direction may be parallel to an optical axis of the objective lens. The surgical microscope may further comprise a transparent protecting plate, which is arranged between the object and components of the microscope. The transparent protecting plate may be designed such as to protect said components from accidental touching and/or staining According to exemplary embodiments, the protecting plate is oriented such that a surface normal of a main surface of the protecting plate and the optical axis of the objective lens form an angle of 15° or more. According to a further exemplary embodiment, the surface normal of the main surface of the protecting plate and the optical axis of the objective form an angle, which is less than 25°, in particular less than 20°.

BRIEF DESCRIPTION OF THE DRAWINGS

The foregoing as well as other advantageous features of the invention will be more apparent from the following detailed description of exemplary embodiments of the invention with reference to the accompanying drawings. It is noted that not all possible embodiments of the present invention necessarily exhibit each and every, or any, of the advantages identified herein.

FIGS. 4a to 4f show diagrams, which illustrate polarization states of measuring light, such as they may occur in a system according to an embodiment shown in FIG. 1;

FIGS. 5a to 5f show diagrams, which illustrate polarization states of measuring light, such as they may occur in a system according an embodiment shown in FIG. 1;

DETAILED DESCRIPTION OF SPECIFIC EMBODIMENTS

Figure 1:
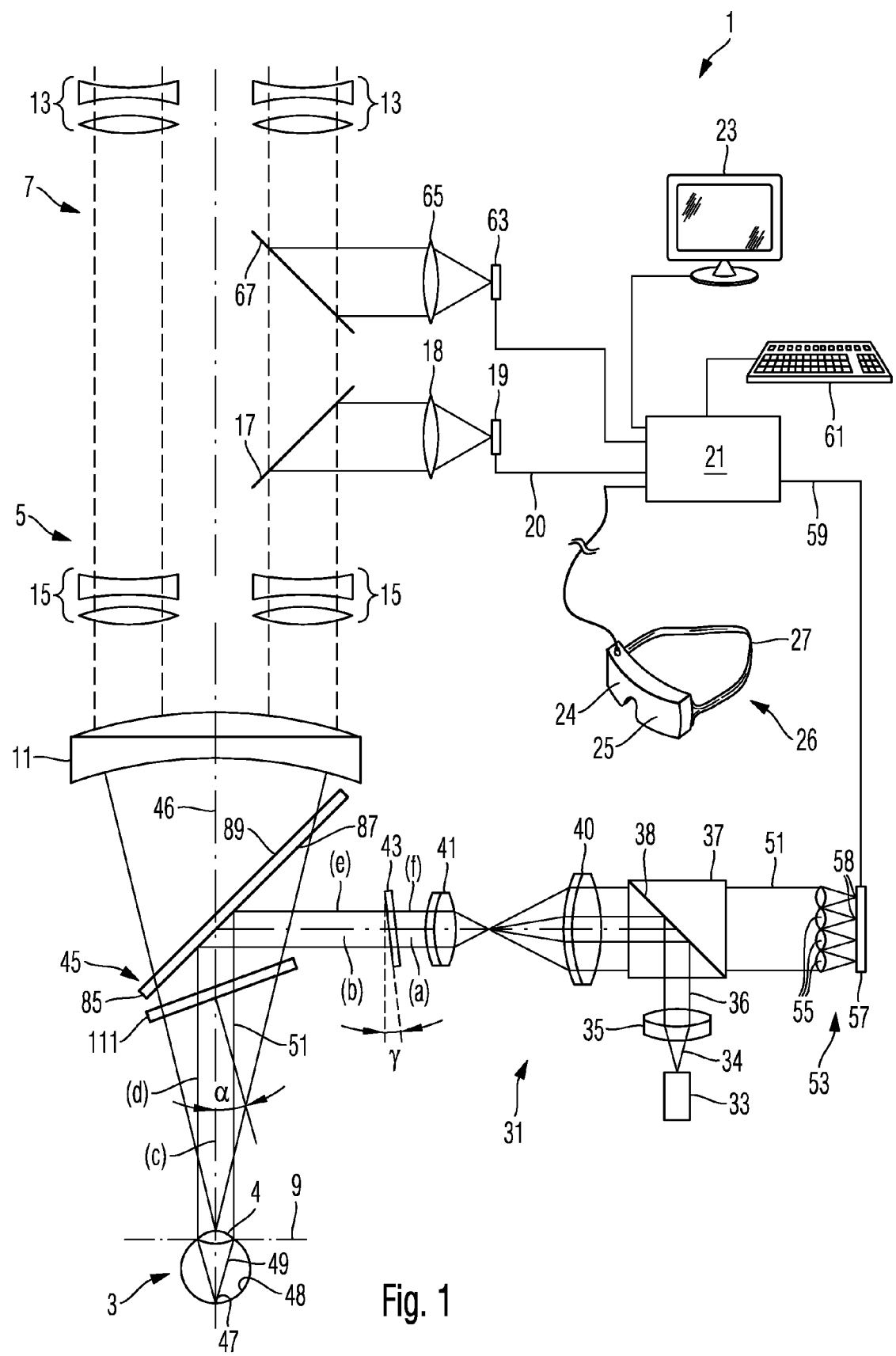
FIG. 1 schematically illustrates the set-up and the operation of an optical system according to an embodiment.

In the exemplary embodiments described below, components that are alike in function and structure are designated as far as possible by alike reference numerals. Therefore, to understand the features of the individual components of a specific embodiment, the descriptions of other embodiments and of the summary of the invention should be referred to.

FIG. 1 shows an eye surgery system 1 for observation of an eye 3 under surgery in a very schematic way. The schematic illustration shows the functionality of the system and also the beam paths, which are designed to provide said functionality in an optical system 5. The optical system 5 comprises a microscope optical system 7, which is designed to provide a magnified image of a portion of the eye 3, which is located in the object plane 9 of the microscope optical system 7. The microscope optical system 7 comprises an objective lens 11 which may include one or more lens elements and two oculars 13. The lens elements and the oculars 13 are arranged downstream of the objective 11. Through the oculars 13, a user can view a magnified image of the object plane 9. The optical system 7 may further comprise zoom systems 15, such that a magnification of the optical system 7 may be variable. The zoom systems 15 may be arranged between the objective lens 11 and the oculars 13.

A semi-transparent mirror 17 may be arranged in the beam paths downstream the objective 11. The semi-transparent mirror 17 may be designed to decouple a portion of the light from the beam path and direct it onto a camera chip 19 via an optical system 18. Intensities of light, which are detected by the camera chip 19, are transmitted in the form of electrical signals via data line 20 to the controller 21. The controller 21 transforms the received data into suitable image data such that it may be recorded and visualized via a display. The display may comprise a monitor 23 and/or displays 24, 25, which are arranged in a head-mounted display device 26. The head-mounted display device 26 may be designed such that it is mountable on a user's head by a belt 27.

The system 1 further comprises a wavefront measuring system 31, which is designed to measure the characteristics of a lens 4 of the eye 3. For example, the wavefront measuring system 31 may be designed to measure aberrations of the lens 4.

The wavefront measuring system 31 comprises a measuring light source 33, which, for example, may be a laser diode. The measuring light source 33 emits measuring light 34, which is collimated by a collimator 35 to a beam 36. The beam 36 enters a beam splitter cube 37, which comprises a splitter layer 38. A certain portion of the measuring light 36 is reflected at the splitter layer 38. This certain portion comprises linearly polarized light, wherein the direction of polarization of said linearly polarized light is determined by properties of the splitter layer 38. Said properties of the splitter layer 38 may comprise, for example, the orientation of the splitter layer 38 with respect to the measuring light 36.

The measuring light 36, which is reflected at the splitter layer 38 traverses two lenses 40, 41, each of them may comprise one or more lens elements. In the described embodiment, the two lenses 40, 41 are designed to form a Kepler telescope, which is configured to transform the measuring light with respect to collimation and cross-section of the beam. The lenses 40, 41 substantially do not influence the state of polarization of the measuring light 36. In addition to the lenses 40, 41, further lenses may be arranged in the beam path downstream of the splitter layer 38, in particular between the splitter layer 38 and the eye 3, for transforming the measuring beam. The lenses 40, 41 may also be designed to form an optical system different from a Kepler telescope, such as, for example, a Galilei telescope.

A retarding plate 43 is arranged in the beam path downstream of the lens 41, which is traversed by the linearly polarized measuring light and is transformed into elliptically polarized measuring light.

The elliptically polarized measuring light is reflected at a dichroic splitting mirror 45, such that it is directed to the eye 3 along an optical axis 46 of the objective lens 11. The elliptically polarized measuring light is focused through the lens 4 of the eye 3 to a spot 47 on the retina 48 of the eye 3. A portion of the measuring light, which is incident on the spot 47 is reflected at the retina 48, wherein a handedness of the circular polarization is reversed. In other words, the direction of the circular polarization is reversed such that, for example, left-handed circularly polarized measuring light is transformed into right-handed circularly polarized measuring light.

The measuring light, which emanates from the spot 47 in the form of a conic light beam 49, is collimated by the lens 4 of the eye 3 to a bundle of rays 51. Assuming an ideal point-like small spot 47, and an error-free imaging of the eye lens 4, the wavefronts in the reflected measuring light 49 are spherical wavefronts and the bundle of rays 51 is a parallel bundle of rays having planar wavefronts. In case the imaging of the eye lens 4 is non-ideal, the wavefronts of the bundle of rays 51 are deformed. The wavefront measuring system 31 is designed such that said deformation is investigated. Thereby, through the analysis of the wavefronts, in particular a refractive error and/or an aberration of the eye lens 4 may be detected.

The bundle of measuring light 51, which travels from the eye 3 towards the objective lens 11 is reflected at the dichroic beam splitter 45 and traverses the retarding plate 43, which transforms the elliptically polarized measuring light into substantially linearly polarized measuring light. The direction of polarization of said substantially linearly polarized measuring light is oriented substantially orthogonal to the direction of polarization of the measuring light 36, which comes from the light source 33 and is polarized through reflection at the splitter layer 38. Due to said orthogonal orientation and also due to the substantially linear polarization of the measuring light, which returns from the eye 3 and which has traversed the telescope 41, 40, the splitter layer 38 of the splitter cube 37 is traversed with comparatively low losses. Thereby, the measuring light, which returns from the object, can enter the wavefront sensor in the form of a bundle of rays 51.

In the schematically illustrated embodiment, the wavefront sensor 53 is a Hartmann-Shack sensor, which comprises an area of micro lenses 55 which are designed to generate an array of focal points 58 on a two-dimensional position sensitive detector 57. The position sensitive detector 57 transmits data signals, which represent detected beam intensities, via a data line 59 to the controller 21. The controller 21 is designed to analyze a deviation of the shape of the wavefront from a planar wave front of the bundle of rays 51 before entering the wavefront sensor 53. Thereby, a refractive error or an aberration of the lens 4 of the eye 3 may be detected.

The controller 21 is connected to a keyboard 61 for operation of the controller 21. The results of the analysis of the wavefronts may be displayed by the controller 21 on a display 23 or on the displays 24, 25. An additional display 63 is connected to the controller 21 for displaying a representation of the analysis. This representation is coupled via an imaging optical system 65 and a coupling-in-mirror 67 into the beam path of the microscope optical system, which travels to the ocular 13. Thereby, a user may view the result of the analysis of the wavefronts while looking into the ocular 13 of the microscope optical system 5.

Figure 2:
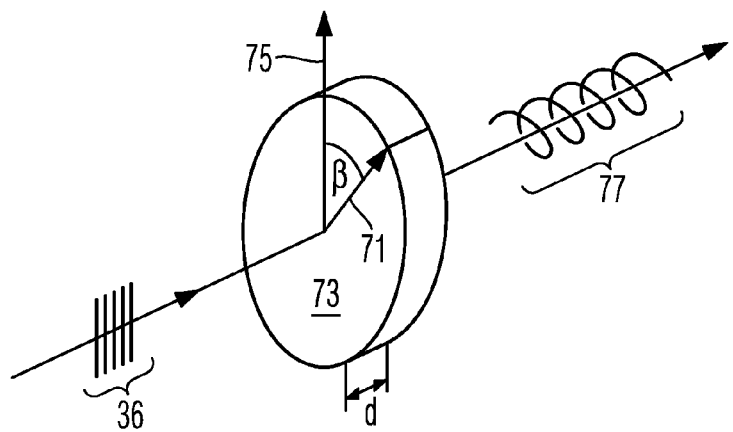
FIG. 2 schematically illustrates an operation of a retarding plate.

The operation of the retarding plate 43 is schematically illustrated in FIG. 2. The retarding plate 43 comprises a plate having a thickness d and being of a birefringent material. The birefringent material has a so-called extraordinary axis. The orientation of the extraordinary axis is shown in FIG. 2 as the vector 71. The plate 43 is cut from birefringent material such that a surface 73 of the plate 43 is oriented parallel to the extraordinary axis 71. The linearly polarized measuring light 36, which has been emitted from the light source 33 and which has passed the polarizing beam splitter 37 is substantially orthogonally incident on the surface 73 of the plate 43. In FIG. 2, the vector 75 denotes the direction of the electrical field vector of the incident linearly polarized measuring light. $\beta$ denotes the angle between the extraordinary axis 71 and the orientation 75 of the polarization of the incident measuring light 36.

A commonly used quarter-wave plate is configured such that for values of $\beta$ of 45°, 135°, 225° and 315° the incident linearly polarized light is transformed exactly into circularly polarized light. Furthermore, for the commonly used quarter-wave plate, the thickness d of the plate is chosen such that between light, which is polarized into the direction 75 and light, which is polarized orthogonal thereto, a relative phase difference of $(2m+1)*\lambda/4$ is generated between said two directions. Herein, $\lambda$ denotes the wavelength of said light and m is an integer. For angles $\beta$, which do not match the values of 45°, 135°, 225°, 315°, the linearly polarized light 36 is not transformed into exactly circularly polarized light, but into elliptically polarized light. In FIG. 2, this is indicated by reference numeral 77. For values of $\beta$, which match the values of 0°, 90°, 180°, 270°, the linear polarization of the light 36 is maintained.

In the following, states of polarization of the measuring light for a system according to FIG. 1 are described with reference to FIG. 3. In said system, a quarter-wave plate is provided as a retarding plate 43, wherein the quarter-wave plate is oriented at an angle of 45° with respect to the direction of polarization of measuring light 36, which comes from the light source 33 and has passed the polarizing beam splitter 37.

FIGS. 3a to 3f respectively show diagrams, which represent amplitudes of the electric field strength of the measuring light for directions x and y at different locations along the beam path. The directions x and y form mutually orthogonal axes, which are both oriented orthogonal to the traveling direction of the beam path.

FIG. 3a shows the amplitudes of the electric field strength Ex and Ey of the linearly polarized measuring light 36, which has been emitted from the light source 33, after having passed the polarizing beam splitter 37 and immediately before entering the quarter-wave plate. The quarter-wave plate is arranged in the beam path as the retarding plate 43. In this example, the measuring light at said location is linearly polarized, which is indicated in FIG. 3a by a horizontal line 81. The diagram of FIG. 3b shows a state of polarization of the measuring light immediately after having passed the quarter-wave plate, wherein the extraordinary axis 71 of the quarter-wave plate is arranged at an angle of 45° with respect to the y-direction. Thereby, the linearly polarized measuring light is transformed into exactly circularly polarized measuring light, as indicated in FIG. 3b by the circle 83.

Then, the measuring light is reflected in the dichroic beam splitter 45. The diagram of FIG. 3c illustrates the state of polarization of the measuring light immediately after having been reflected at the dichroic beam splitter 45. The dichroic beam splitter 45 comprises a transparent plate 85. The plane side 87 of the transparent plate 85, which faces the object, for example the eye 3, carries a coating, which comprises a plurality of dielectric layers. The plurality of dielectric layers is configured such that light having a wave length of the measuring light is reflected thereon. In the example, the light source 33 emits measuring light having a wavelength outside of the visible spectrum and above 800 nm. In an example, where the light source 33 comprises a super luminescence diode (SLD), the measuring light may comprise a wavelength of 830 nm. The coating on the side 87 of the plate 85 is further configured such that visible light traverses the coating with only minimal losses. Thereby, the user may observe the object in the object plane 9 at a high quality by looking into the oculars 13.

Furthermore, surface 89 of the plate 85, which is opposite to the side 87 of the plate 85, may be provided with a dielectric anti-reflection layer, which is configured to reduce reflections of light, which is in the visible range of the spectrum, at the dichroic beam splitter 45.

Although the reflective layer on the surface 87 is configured such that the measuring light is optimally reflected thereon, it is hardly feasible to reflect both directions of polarization of the measuring light and maintaining their relative phase. Therefore, the circularly polarized measuring light, which exits the quarter-wave plate is transformed into elliptically polarized light by the reflection at the dichroic beam splitter 45, as shown in FIG. 3c by the ellipse 91.

The elliptically polarized measuring light is reflected at least partly at the retina 48 of the eye 3, wherein the elliptically state of polarization is maintained and the handedness of the elliptical polarization is reversed. FIG. 3d illustrates the state of polarization in the beam path of the measuring light after being reflected at the retina 48 of the eye 3 and before again impinging at the dichroic beam splitter 45. The ellipse 93 represents the state of polarization with reversed handedness with respect to the ellipse 91.

The ellipse 95, which is shown in FIG. 3e represents the state of polarization of the measuring light, which returns from the eye 3, after having passed the dichroic beam splitter 45 and before entering the quarter-wave plate. Comparing the ellipse 93 and the ellipse 95 it is apparent that the reflective layer of the surface 87 has further changed the state of polarization of the measuring light. In particular, the eccentricity of the ellipse has increased.

After having been reflected at the dichroic beam splitter 45, the more pronounced elliptically polarized measuring light is transformed into linearly polarized light by the quarter-wave plate, as shown by the line 97 in FIG. 3f. The line 97, however, is not oriented strictly along the y-direction, but is inclined relative to the y-direction. However, only the component of light 97, which is oriented parallel to the y-direction, passes the polarizing beam splitter 37 and arrives at the wave front sensor 53. The component of light 97 which is oriented parallel to the x-direction is lost at the beam splitter 37.

In order to overcome this disadvantage, an embodiment, which is described in the following is provided with a retarding plate 43, which is arranged in the beam path such that the extraordinary axis of the birefringent material is not oriented at an angle of 45°, 135°, 225° or 315° relative to the direction of polarization of the measuring light. Rather, the quarter-wave plate is rotated at a suitable angle relative to an angle of 45°, 135°, 225° or 315°, respectively, as explained with reference to FIG. 4. Furthermore, the extraordinary axis may be set such that it is not rotated at angles of 0°, 90°, 180° and 270° relative to the direction of polarization of the measuring light.

FIGS. 4*a* to 4*f* correspond to the diagrams of FIGS. 3*a* to 3*f*, represent the state of polarization of the measuring light at different locations along the beam path.

In FIG. 4*a*, the line 81 represents the linearly polarized measuring light 36 coming from the polarizing beam splitter 37 and prior to entering the quarter-wave plate. The quarter-wave plate is rotated with respect to an orientation of 45°, i.e. it deviates from an orientation of 45° by a predetermined angle. The quarter-wave plate does therefore not exactly generate circularly polarized light from the measuring light 36 coming from the polarizing beam splitter 37. Rather, elliptically polarized light is generated, as shown by the ellipse 83 in FIG. 4*b*. Ellipse 83 of FIG. 4*b* is transformed into ellipse 91 of FIG. 4*c* after reflection at the dichroic beam splitter 45 and prior to impinging on the object. Ellipse 93 of FIG. 4*d* represents the state of polarization of the measuring light, which is returning from the object with an reversed handedness. This light is transformed by a further reflection at the dichroic beam splitter 45 into light, which has a state of polarization, which is represented by ellipse 95 in FIG. 4*e*. This light, after having traversed the quarter-wave plate, which is rotated with respect to 45°, is transformed into light having a state of polarization, which is represented by an ellipse 97 in FIG. 4*f*. It is apparent from FIG. 4*f* that the maximum field vector of this light is oriented along the y-direction. Thereby, this light can traverse the polarizing beam splitter 37 to a large extent for efficiently being detected by the wavefront sensor 53. Compared to the situation as shown in FIG. 3*f*, an increase of the detected intensity of measuring light has been achieved. However, a small portion of the measuring light can not be detected by the wavefront sensor 53, since the line 97 is elliptical to a small extent and the electric field strength still comprises a component along the x-direction.

The retarding plate 43 may further be modified with respect to the above-described quarter-wave plate in order to further suppress the x-component of the electrical field of the measuring light returning from the object and prior to entering the polarizing beam splitter 37. This is described in the following with reference to FIG. 5.

The retarding plate 43 may be designed such that the phase difference provided by the retarding plate 43 for the measuring light deviates from the value of λ/4. In particular, the thickness of the plate is adapted to the refractive index of the birefringent material such that the provided phase shift deviates from values of λ/4, 3λ/4, etc. Furthermore, the retarding plate is arranged such that the direction of the extraordinary axis of the retarding plate 43 relative to the direction of polarization of the light, which comes from the light source 33, deviates from values of 45°, 135°, 225° and 315.

FIG. 5*b* illustrates the state of polarization of the measuring light coming from the light source 33 and having passed the retarding plate 43 with an adapted thickness, as described above. The ellipse 83, as shown in FIG. 5*b*, is rotated to a small extent, compared to the ellipse 83 shown in FIG. 4*b*. This change in the state of polarization after having passed the retarding plate 43 results in a polarization of the measuring light exactly along the y-direction when returning from the object and prior to entering the polarizing beam splitter 37. This is shown as the line 97 in FIG. 5*f*. The linearly polarized measuring light of FIG. 5*f* can traverse the beam splitter 37 with minimal losses. Thereby a maximum of intensity can be detected by the wavefront sensor 53.

Figure 3:
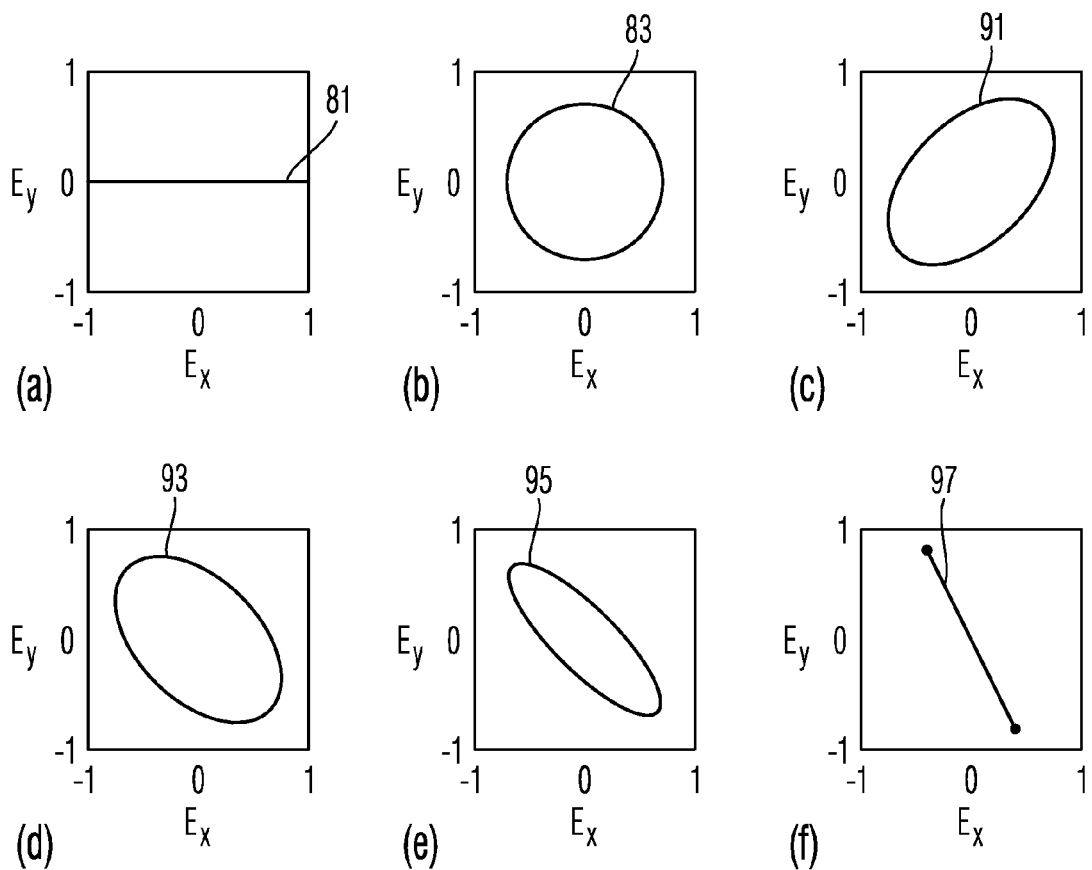
FIGS. 3a to 3f show diagrams which illustrate polarization states of the measuring light, such as they may occur in a system according to an embodiment shown in FIG. 1.

Comparing FIGS. 3, 4 and 5, it is demonstrated that by modifying the commonly used combination of a polarizing beam splitter and a quarter-wave plate, measuring light can be detected with an increased intensity, in case, for example, a dichroic beam splitter or other components which modify the state of polarization of the measuring light are arranged in the beam path. According to the commonly used combination comprising a polarizing beam splitter and a quarter-wave plate, the extraordinary axis of the quarter-wave plate is oriented at an angle of 45°, 135°, 225° or 315° relative to the electrical field vector of the linearly polarized light coming from the polarizing beam splitter 37, wherein the quarter-wave plate provides a phase shift of λ/4, 3λ/4 etc.

Figure 6:
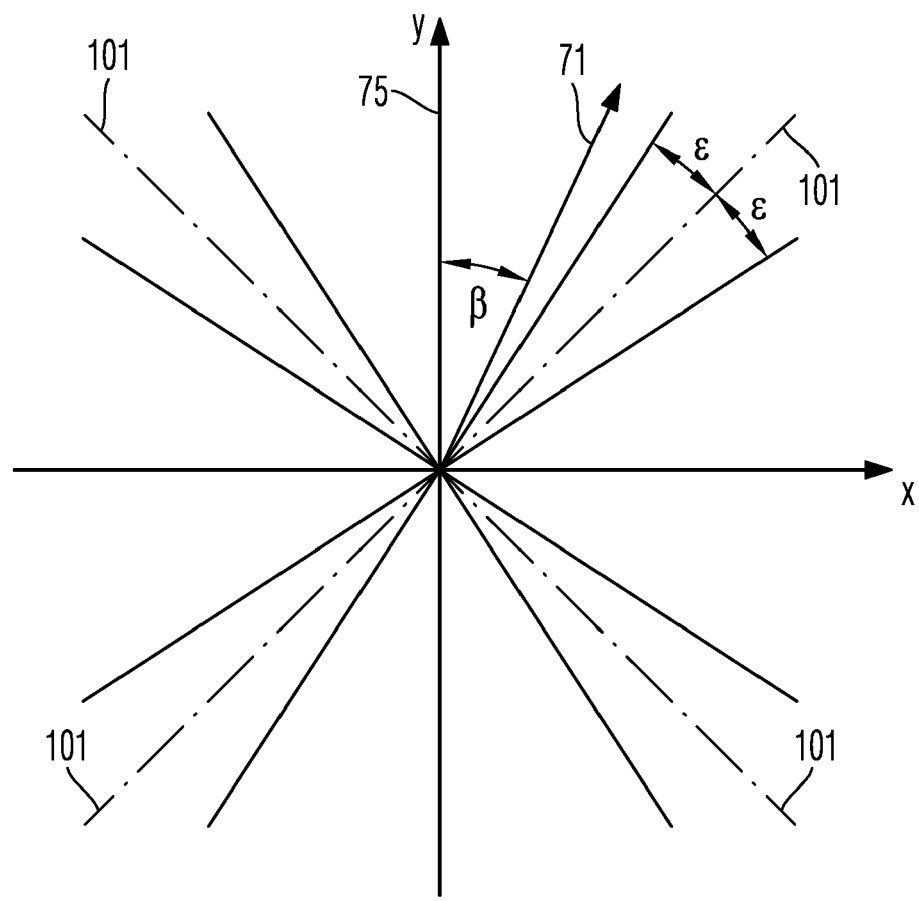
FIG. 6 shows a schematic illustration of possible orientations of a retarding plate according to embodiments.

According to embodiments, an extraordinary axis of a material of a retarding plate is rotated by more than 4° relative to an angle of 45° (or an angle of 135°, 225° or 315°, respectively) with respect to the direction of polarization of the linearly polarized light which exits the polarizing beam splitter. The angle between the extraordinary axis of the retarding plate and the direction of polarization of the linearly polarized light further may be set such that it does not match values of 90°, 180° and 270°. This design rule is further schematically illustrated in FIG. 6. There, the lines 110 are oriented at angles of 45, 135°, 225° and 315° with respect to, for example, the x-axis of the coordinate system. ε denotes angles, which are greater than 4° and which are less than 45°. Vector 71 in FIG. 6 represents an orientation of the extraordinary axis of the birefringent material of the retarding plate 43 relative to the electric field vector 75 of the impinging linearly polarized measuring light. In FIG. 6, the electrical field vector 75 is oriented along the y-direction.

The acceptable values for the angle β formed by the electrical field vector 75 and the orientation 71 of the extraordinary axis of the material may thereby be given by the equation $$(2n+1)*45°+\epsilon \leq \beta \leq (2n+3)*45°-\epsilon$$

wherein n represents an integer; and

ε represents a value greater than 4° and less than 45°.

According to further embodiments the value of ε may be greater than for example 6°, 8° or 10°.

The value for β may further not match values of 0°, 90°, 180° and 270°.

Figure 7:
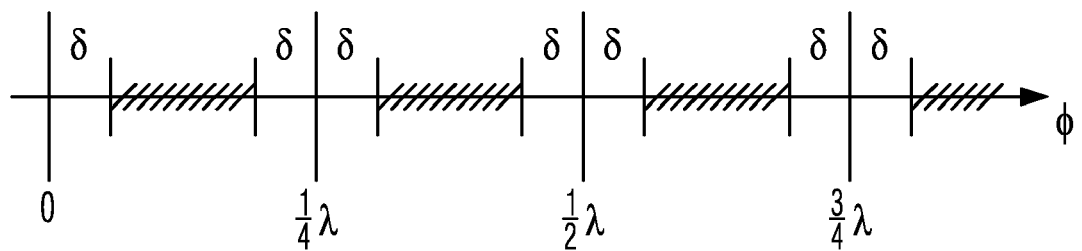
FIG. 7 shows a schematic illustration of possible phase shifts provided by a retarding plate according to embodiments.

As can be seen by comparing FIGS. 5 and 3, modifying the phase shift provided by the retarding plate 43 relative to a value of λ/4 may further lead to an increase of the intensity of the detectable measuring light. The possible values for the phase difference φ, provided by the retarding plate 43, are shown in FIG. 7. According to the diagram of FIG. 7, the possible values for the phase shift φ may lie in ranges of from 0+δ to ¼λ−δ, from ¼λ+δ to ½λ−δ, from ½λ+δ to ¾λ−δ etc.

These ranges for the phase difference φ may be given by the following formula $$(2m)\lambda/4+\delta \leq \phi \leq (2m+1)\lambda/4-\delta,$$

wherein

λ represents a wavelength of the light, m represents an integer

δ represents a value greater than 0.05*λ/4 and less than λ/8.

According to further embodiments, the lower level for the range of values of φ may be set higher, for example 0.1*λ/4, or 0.15*λ/4.

In the following, reference is made to FIG. 1. A transparent protecting plate 111, is arranged between the object 3 and components of the microscope, wherein the protecting plate 111 is designed to protect said components from accidentally touching, damaging and/or staining In particular, the protecting plate 111 may be designed such that the coating of the dichroic beam splitter 45 is protected from staining caused by the object under investigation. The protecting plate 111 is arranged inclined by a predetermined angle α with respect to the beam path, which traverses the protecting plate 111. Thereby, the surface normal of the protecting plate 111 and the optical axis 46 of the objective 11 form an angle α, which may be more than 5°. Accordingly, portions of the measuring light, which are reflected at the protecting plate 111 are not redirected into the respective beam path and, hence, are prevented from being detected as noise signals.

For similar reasons, the retarding plate 43 is inclined at a predetermined angle γ with respect to a direction, which is oriented orthogonal to the direction of the beam path. The predetermined angle γ may be small.

In the previously described embodiment, the dichroic beam splitter is linearly traversed by the observation beam path having light in the visible range. The measuring light path, having wavelengths above 800 nm, is reflected at the dichroic beam splitter. However, it is also possible that the measuring beam path is linearly traversing the dichroic beam splitter whereas the microscopic observation beam path is reflected at the dichroic beam splitter.

According to the above-described embodiment, the light detector of the measuring beam path is a wavefront detector. Alternatively or additionally, a different type of detector is provided in the measuring beam path, wherein said different type of detector may serve purposes, which are different from the detection of wave fronts.

The wavefront sensor as described in conjunction with the above-described embodiment is of a Hartmann-Shack type. Additionally or alternatively, wave front sensors of a different type may be provided in combination with the embodiments.

In the above-described embodiment, three beam paths are separated from each other by a dichroic beam splitter and a polarizing beam splitter, wherein one beam path has light within the visible range and the other beam paths are of light beyond 800 nm. Alternatively, different, non-overlapping ranges of wavelengths may be used.

In the above-described embodiment, the functionality of the surgical microscope is combined with the functionality of a wavefront sensor. Additionally or alternatively, other functionalities of different optical systems, which comprise dichroic and polarizing beam splitters, may be combined. In particular, the embodiments are not limited to the field of eye surgery.

According to embodiments, a system comprises a dichroic beam splitter, a polarizing beam splitter and a retarding plate. The retarding plate may be arranged in the beam path such that an orientation of an extraordinary axis of the retarding plate is rotated with respect to angles of 45°, 135°, 225° and 315° relative to a direction of polarization of light, which traverses the retarding plate. Additionally or alternatively, the retarding plate may provide a relative phase difference, which is different from values of ¼λ, ½λ, ¾λ etc.

While the invention has been described with respect to certain exemplary embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

What is claimed is:

1. An eye surgery system for observing an object with an optical system, wherein the eye surgery system is configured to provide a first beam path for light of a first range of wave lengths and to provide a second beam path and a third beam path for light of a second range of wave lengths, wherein the object is arranged in the first, second and third beam paths and wherein the optical system comprises a dichroic beam splitter, a polarizing beam splitter and a retarding plate, wherein the eye surgery system is configured such that (a) the first beam path traverses the dichroic beam splitter and the second and the third beam paths are reflected at the dichroic beam splitter, or (b) the second and third beam paths traverse the dichroic beam splitter and the first beam path is reflected at the dichroitic beam splitter, wherein the eye surgery system is further configured such that (c) the second beam path traverses the polarizing beam splitter and the third beam path is reflected at the polarizing beam splitter, or (d) the third beam path traverses the polarizing beam splitter and the second beam path is reflected at the polarizing beam splitter, and wherein the retarding plate is of a birefringent material having an extraordinary axis, wherein the retarding plate is arranged in the second and third beam paths and between the object and the polarizing beam splitter, and wherein the retarding plate is configured such that at least one of the following relations is fulfilled:

(e) for light, which is polarized along the extraordinary axis, and light, which is polarized substantially orthogonal to the extraordinary axis, a relative phase difference is provided, which satisfies:

$$(2m)\lambda/4 + \delta \leq \phi \leq (2m+1)\lambda/4 - \delta,$$

wherein

λ is a wavelength of the light,

φ is the phase difference m is an integer, and

δ represents a value greater than $0.05 * \lambda/4$ and less than $\lambda/8$, and (f) the extraordinary axis of the birefringent material has an angle relative to the direction of polarization of the light of the second beam path, which has traversed or is reflected at the polarizing beam splitter, wherein the angle satisfies:

$$(2n+1)*45° + \epsilon \leq \beta \leq (2n+3)*45° - \epsilon$$

wherein:

β represents the angle, n represents an integer, and

ε represents a value greater than 4° and less than 45°.

2. The eye surgery system according to claim 1, wherein the optical system comprises an objective lens, which is arranged in the first beam path and which is configured to image the object.

3. The eye surgery system according to claim 2, wherein the optical system comprises at least one ocular, which is arranged in the first beam path and downstream of the objective lens and/or wherein the optical system further comprises a camera, which is arranged in the first beam path and downstream of the objective lens and a display which is configured to display an image of the object to a user.

4. The eye surgery system according to claim 1, wherein the optical system comprises a measuring light source, which is arranged in the second beam path and which is configured to illuminate the object with measuring light.

5. The eye surgery system according to claim 1, wherein the optical system comprises a measuring light detector, which is arranged in the third beam path and which is configured to detect measuring light, which emanates from the object.

6. The eye surgery system, according to claim 5, wherein the measuring light detector comprises a wavefront detector.

7. The eye surgery system according to claim 6, wherein the wavefront detector comprises an Hartmann-Shack type sensor.

8. The eye surgery system according to claim 5, further comprising a controller, which is configured to analyze detection signals, which are generated by the measuring light detector and wherein the controller is further configured to provide an analysis result.

9. The eye surgery system according to claim 8, further comprising a display, which is configured to display the analysis result.

10. The eye surgery system according to claim 9, wherein the display is configured to superimpose the display of the analysis result with a beam path of an ocular of the eye surgery system.

11. The eye surgery system according to claim 1, wherein the optical system comprises at least one lens, arranged in the second and third beam paths and between the dichroic beam splitter and the polarizing beam splitter.

12. The eye surgery system according to claim 11, wherein the at least one lens is arranged between the retarding plate and the polarizing beam splitter.

13. The eye surgery system according to claim 11, wherein the at least one lens forms a Kepler telescope or a Galilei telescope.

14. The eye surgery system according to claim 1, wherein the eye surgery system is designed such that the dichroic beam splitter is traversed by the first beam path and wherein the dichroic beam splitter comprises a transparent plate, which is transparent for the light of the first range of wavelengths.

15. The eye surgery system according to claim 14, wherein the transparent plate carries a dielectric reflective coating on a surface of the transparent plate, which faces the object, and wherein the dielectric reflective coating is reflective for the light of the second and the third beam paths.

16. The eye surgery system according to claim 14, wherein the transparent plate carries a dielectric anti-reflective coating on a surface of the transparent plate, which is averted from the object, wherein the dielectric anti-reflective coating is anti-reflective for the light of the first beam path.

17. The eye surgery system according to claim 1, wherein a transparent protecting plate having two parallel surfaces is arranged in the first, the second and the third beam path and between the dichroic beam splitter and the object.

18. The eye surgery system according to claim 17, wherein an angle between a surface normal of the surfaces of the protecting plate and a main axis of the second beam path is greater than 5°.

19. The eye surgery system according to claim 1, wherein the light of the first range of wavelengths comprises visible light.

20. The eye surgery system according to claim 1, wherein the first range of wavelengths comprises wavelengths between 450 nm and 700 nm.

21. The eye surgery system according to claim 1, wherein the second range of wavelengths comprises wavelengths greater than 800 nm.

* * * * *